United States Patent
Munsell et al.

(10) Patent No.: US 9,763,438 B2
(45) Date of Patent: Sep. 19, 2017

(54) PEST POST RAT REPELLENT SYSTEM

(71) Applicants: Clyde Stephan Munsell, Chula Vista, CA (US); James Dalgleish Reid, San Diego, CA (US); Richard William Hanawalt, Ventura, CA (US)

(72) Inventors: Clyde Stephan Munsell, Chula Vista, CA (US); James Dalgleish Reid, San Diego, CA (US); Richard William Hanawalt, Ventura, CA (US)

(73) Assignee: STICK-IN-THE-MUD LLC, Chula Vista, CA (US)

( * ) Notice: Subject to any disclaimer, the term of this patent is extended or adjusted under 35 U.S.C. 154(b) by 0 days.

(21) Appl. No.: 14/510,972

(22) Filed: Oct. 9, 2014

(65) Prior Publication Data
US 2015/0208638 A1   Jul. 30, 2015

Related U.S. Application Data

(60) Provisional application No. 61/913,197, filed on Dec. 6, 2013.

(51) Int. Cl.
| | | |
|---|---|---|
| *A61K 36/534* | (2006.01) | |
| *A61K 36/889* | (2006.01) | |
| *A01M 29/12* | (2011.01) | |
| *A01N 25/18* | (2006.01) | |
| *A01N 25/34* | (2006.01) | |
| *A01N 65/22* | (2009.01) | |

(52) U.S. Cl.
CPC ............ *A01M 29/12* (2013.01); *A01N 25/18* (2013.01); *A01N 25/34* (2013.01); *A01N 65/22* (2013.01)

(58) Field of Classification Search
None
See application file for complete search history.

(56) References Cited

U.S. PATENT DOCUMENTS

| | | | |
|---|---|---|---|
| 3,791,346 | A | 2/1974 | Willinger et al. |
| 4,157,696 | A | 6/1979 | Carlberg |
| 4,735,803 | A | 4/1988 | Katz et al. |
| 4,775,532 | A | 10/1988 | Clayton |
| 4,940,583 | A | 7/1990 | Thompson |
| 5,242,111 | A | 9/1993 | Nakoneczny et al. |
| 5,344,649 | A | 9/1994 | Mungia |
| 5,372,429 | A | 12/1994 | Beaver, Jr. et al. |
| 5,571,522 | A | 11/1996 | Munson et al. |
| 5,674,496 | A | 10/1997 | Etscorn et al. |
| 5,714,445 | A | 2/1998 | Trinh et al. |
| 5,798,385 | A | 8/1998 | Marin |
| 7,575,765 | B1 * | 8/2009 | Hughes ................ A61K 36/00 424/725 |
| 2003/0108582 | A1 * | 6/2003 | Willis .................. A01N 65/00 424/405 |

OTHER PUBLICATIONS

Website document entitled: "Murphy's Mosquito Stickes" (available at http://www.murphysnaturals.net/murphysmousquitosticks). Downloaded from website Jan. 1, 2016.*
Website document entitled Amazon.com: Murphy's Mosquito Sticks (available at http://www.amazon.com/Murphys-Mosquito-Sticks-Citronella-Lemongrass . . . ). Downloaded from website Jan. 7, 2016. The reviews indicate that the product was commercially available prior to filing date of invention.*
Website document entitled "Amazon.com: Repel 4263 Insect Repellent Stakes" (available at http://www.amazon.com/Repel-4263-Insect-Repellent-Stakes . . . ). Downloaded from website Jan. 7, 2016.*
Alankar (2009) Asian Journal of Pharmaceutical and Clinical Research, vol. 2, Issue 2, pp. 27-33.*
Ansari et al. (2000) Bioresource Technology 71: 267-271.*
Website document entitled: "Fractionated Coconut Oil" (available at https://www.organicfacts.net/health-benefits/oils/fractionated-coconut-oil.html). Downloaded from website Jan. 7, 2016.*
Wesite document entitled: "How to Use Peppermint to Repel Mice" (available at http://www.ehow.com/how_8330912_use-peppermint-repel-mice.html). Downloaded Jan. 7, 2016.*

* cited by examiner

*Primary Examiner* — Chris R Tate
*Assistant Examiner* — Russell Fiebig
(74) *Attorney, Agent, or Firm* — Garrett O'Sullivan; Eric Lovell; Marc Shropshire

(57) ABSTRACT

A rodent repellent system for repelling rodents from open spaces while simultaneously providing a pleasant scent. The inventive device includes a wood stake which is driven into the ground. The stake is soaked in a fragrance oil. A package preferably stores one or more of the stakes preferably within a sealable plastic bag. The user drives the stake into open earth in the area to be cleared of rodents. The fragrance oil is retained by the stake and slowly released. The fragrance oil provides a strong scent that repels rodents by irritating their respiratory system while simultaneously providing a pleasant scent to humans.

4 Claims, No Drawings

PEST POST RAT REPELLENT SYSTEM

BACKGROUND OF THE INVENTION

1. Field of the Invention

The present invention relates generally to repellent systems and more specifically it relates to a rodent repellent system for repelling rodents in open areas while simultaneously providing a pleasant scent.

Rodents such as mice and rats are a common problem in open areas. Rodents destroy foliage, carry diseases harmful to both humans and pets, and often infiltrate tractors, trucks, recreational vehicles, boats, implements, and buildings. Rodents can cause significant damage to foliage of all kind, vehicles, irrigation lines, and present a risk of disease to humans and animals. Hence, there is a need for a system that repels rodents while simultaneously providing a pleasant scent for most humans.

2. Description of the Prior Art

Rodent repellent systems have been in use for years. Outdoor systems typically require a power source to be effective, such as sonic or heat activated systems. Other common products utilized to control rodents are poisonous products such as D-Con. However, poison can be harmful to children if swallowed or touched. In addition, the rodents often die in the area causing an undesirable odor and health hazard if they are eaten by a pet or must be disposed of.

Examples of rodent related devices and system include U.S. Pat. No. 4,735,803 to Katz et al; U.S. Pat. No. 4,775,532 to Clayton; U.S. Pat. No. 5,372,429 to Beaver, Jr. et al; U.S. Pat. No. 4,940,583 to Thompson; U.S. Pat. No. 5,714,445 to Trinh et al; U.S. Pat. No. 5,674,496 to Etscorn et al; U.S. Pat. No. 5,571,522 to Munson et al; U.S. Pat. No. 5,344,649 to Mungia; U.S. Pat. No. 5,242,111 to Nakoneczny et al; U.S. Pat. No. 4,157,696 to Carlberg; U.S. Pat. No. 3,791,346 to Willinger et al; U.S. Pat. No. 5,798,385 to Marin which are all illustrative of such prior art.

While these devices may be suitable for the particular purpose to which they address, they are not as suitable for repelling rodents from open areas while simultaneously providing a pleasant scent without the need for a power source.

In these respects, the rodent repellent system according to the present invention substantially departs from the conventional concepts and designs of the prior art, and in so doing provides an apparatus primarily developed for the purpose of repelling rodents from an open area while simultaneously providing a pleasant scent. Another object is to provide a rodent repellent system that has an EPA minimum risk classification to humans.

SUMMARY OF THE INVENTION

In view of the foregoing disadvantages inherent in the known types of repelling systems now present in the prior art, the present invention provides a new rodent repellent system construction wherein the same can be utilized for repelling rodents from open areas while simultaneously providing a pleasant scent.

The general purpose of the present invention, which will be described subsequently in greater detail, is to provide a new rodent repellent system that has many of the advantages of the repelling systems mentioned heretofore and many novel features that result in a new rodent repellent system which is not anticipated, rendered obvious, suggested, or even implied by any of the prior art repelling systems, either alone or in any combination thereof.

To attain this, the present invention generally comprises a wooden stake soaked in a fragrant combination of oils. A package stores one or more of the stakes within a sealable plastic bag. The user removes a single post and drives the stake into the ground in the area intended to be protected from rodents. The fragrance oil permeates the wooden stake and is slowly released to the surrounding atmosphere. The fragrance oil provides a strong scent that repels rodents by irritating their respiratory system while simultaneously providing a pleasant scent to humans.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a rodent repellent system that will overcome the shortcomings of the prior art devices.

Another object is to provide a rodent repellent system that effectively repels rodents from open areas.

An additional object is to provide a rodent repellent system that is pleasant smelling to most individuals.

A further object is to provide a rodent repellent system that is a respiratory irritant to rodents.

Another object is to provide a rodent repellent system that is has an EPA minimum risk classification to humans.

An additional object is to provide a rodent repellent system that does not harm rodents or humans.

A further object is to provide a rodent repellent system that is easily placed in an open area.

Another object is to provide a rodent repellent system that is comprised of natural substances.

Other objects and advantages of the present invention will become obvious to the reader and it is intended that these objects and advantages are within the scope of the present invention.

To the accomplishment of the above and related objects, this invention may be embodied in the form illustrated in the accompanying description, attention being called to the fact, however, changes may be made in the specific construction described within the scope of the appended claims.

DESCRIPTION OF THE PREFERRED EMBODIMENT

Turning now descriptively to the invention, which comprises a wooden stake permeated by a fragrance oil having a woodsy floral blend. The stake is composed of Medium Density Fiberboard (MDF) and wedge shaped, approximately 8 inches long ½ inch wide and tapered from 2 inches across on one end to a point on the other end. During manufacture the stake is soaked in a heated combination of Crystal Menthol, peppermint oil, and fractionated coconut oil, the coconut oil used as a surfactant to aid in absorption and provide for even evaporation of the fragrance when used by the consumer. A package stores one or more of the stakes within a sealable plastic bag. The user removes a stake from the package and drives the stake into the ground in the area to be cleared of rodents, leaving sufficient surface area exposed to the air to allow for the oil to evaporate into the surrounding atmosphere over time. The fragrance oil is retained by the stake and slowly released through the air. The fragrance oil provides a strong scent that repels rodents by irritating their respiratory system while simultaneously providing a pleasant scent to humans. After the scent is weakened over time, the user simply removes the old stake and replaces it with a new one.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of repelling rats from an area comprising the steps of:
   (a) soaking a section of medium density fiberboard (MDF) shaped as a stake in a solution comprising effective amounts of Crystal Menthol, peppermint oil, and fractionated coconut oil for a duration of time to permeate the MDF to saturation with the solution to produce a saturated stake; and
   (b) positioning the saturated stake within the area to be cleared of rats, wherein the stake is approximately 8 inches long, ½ inch thick, and tapered from 2 inches across on one end to a point on an opposite end, whereby rats are effectively repelled from said area.

2. The method of claim 1, wherein the solution irritates a respiratory system of the rats.

3. The method of claim 1, wherein the stake is driven into the ground, wherein a surface area of the stake is exposed to air, wherein a scent of the solution is released into the atmosphere.

4. The method of claim 1, wherein the solution is heated.

* * * * *